United States Patent [19]

Wu

[11] Patent Number: 5,633,380
[45] Date of Patent: May 27, 1997

[54] SUBSTITUTED QUINOLINE HERBICIDE INTERMEDIATES AND PROCESS

[75] Inventor: Wen-Xue Wu, Mercer, N.J.

[73] Assignee: American Cyanamid Company, Madison, N.J.

[21] Appl. No.: 461,786

[22] Filed: Jun. 5, 1995

[51] Int. Cl.$^6$ .................. C07D 215/12; C07D 215/14; C07D 215/38
[52] U.S. Cl. .................. 546/174; 546/175; 546/176
[58] Field of Search .................. 546/176, 178, 546/174, 175

[56] References Cited

U.S. PATENT DOCUMENTS

| | | | |
|---|---|---|---|
| 3,297,525 | 1/1967 | Grier | 167/58 |
| 3,362,960 | 1/1968 | Hodel | 260/287 |
| 5,288,866 | 2/1994 | Strong | 544/215 |
| 5,378,843 | 1/1995 | Strong | 544/215 |

FOREIGN PATENT DOCUMENTS

| | | |
|---|---|---|
| 1450570 | 8/1966 | France . |
| 936342 | 9/1963 | United Kingdom . |
| 2192877 | 1/1988 | United Kingdom . |

OTHER PUBLICATIONS

Anzini, M.; Cappelli, A; and Vomero, S. *Heterocycle* 1994, vol. 38, 103.

Danishefsky, S.; Bryson, T.A.; and Puthenpurayil, J. *J. Org. Chem.* 1975, vol. 40, 796.

*Primary Examiner*—C. Warren Ivy
*Assistant Examiner*—Evelyn Huang
*Attorney, Agent, or Firm*—Joseph M. Mazzarese

[57] ABSTRACT

The invention is substituted quinoline intermediates useful in the synthesis of the herbicide 2-(4-isopropyl-4-methyl 5-oxo 2-imidazolidinyl)-5-methoxymethylnicotinic acid and a process for preparing the herbicide intermediate 3-methoxymethyl-7- or 8-hydroxyquinoline.

15 Claims, No Drawings

SUBSTITUTED QUINOLINE HERBICIDE INTERMEDIATES AND PROCESS

SUMMARY OF THE INVENTION

The invention is substituted quinoline intermediates useful in the synthesis of the herbicide 2-(4-isopropyl-4-methyl-5-oxo-2-imidazolidinyl)-5-methoxymethylnicotinic acid and a process for preparing the herbicide intermediate 3-methoxymethyl-7- or 8-hydroxyquinoline.

DETAILED DESCRIPTION

The invention is herbicide intermediate compounds of the formula

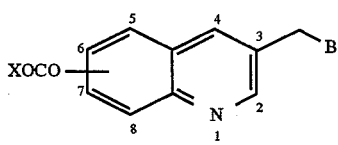

wherein X is straight or branched $C_1$–$C_6$ alkyl, phenyl, —O-phenyl, —O—$C_1$–$C_4$ straight or branched alkyl or

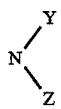

wherein Y and Z are independently H, straight or branched $C_1$–$C_6$ alkyl or phenyl, and B is H, halogen or a quaternary ammonium halide; and a process for preparing compounds of the formula

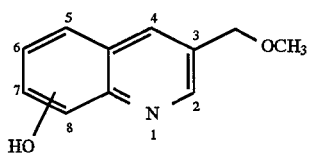

which comprises reacting a compound of the formula

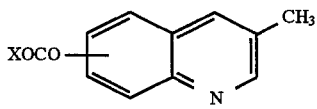

wherein X is a straight or branched $C_1$–$C_6$ alkyl, phenyl, —O-phenyl, —O—$C_1$–$C_4$ straight or branched alkyl or

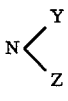

wherein Y and Z are independently H, straight or branched $C_1$–$C_6$ alkyl or phenyl; reacting compound II with a radical halogenating reagent wherein the halogen is bromine or chlorine to form a compound of the formula

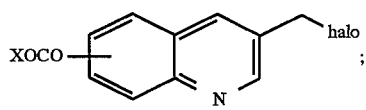

reacting compound III with a tertiary amine without a reactive beta-hydrogen to form a compound of the formula

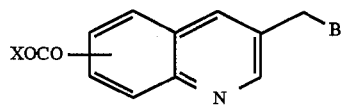

wherein B is a quaternary ammonium halide; and reacting compound IV with a base in methanol at a temperature within the range of about 120° C. to about 180° C. in a closed reactor to form a compound of formula I; or reacting compound IV with a base in methanol in the presence of a transition metal salt at a temperature within the range of about 65° C. to about 180° C. in a closed reactor to form a compound of formula I.

The compound 3-methoxymethyl-8-hydroxy quinoline is useful in the preparation of the 5-methoxymethyl-2,3-pyridinedicarboxylic acid intermediate for the herbicide 2-(4-isopropyl-4-methyl-5-oxo-2-imidazolidinyl)-5-methoxymethylnicotinic acid of U.S. Pat. No. 5,334,576.

The invention is further illustrated in the examples, below, but is not to be deemed limited thereby.

EXAMPLE 1

Preparation of Acylated 8-Hydroxy-3-Methylquinoline

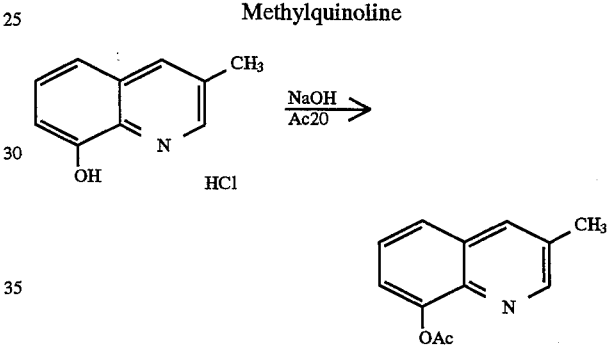

A mixture of the hydrochloride salt of 8-hydroxy-3-methylquinoline (200 g, 1.02 mol) and sodium hydroxide (102 g, 2.55 mol) in 1000 ml water is treated with acetic anhydride (208 g, 2.04 mol) at 0°–10° C. over 1 hour and is allowed to stir at room temperature for 1 hour. An additional portion of acetic anhydride (50 g, 0.49 mol) is added and the resulting mixture is stirred for one more hour. Saturated sodium bicarbonate (100 ml) is added dropwise. The crude product is collected by filtration, washed with water, and dried at 60° C. under vacuum. Recrystalization from ethyl acetate and heptane affords white needles (168.5 g, 82% yield).

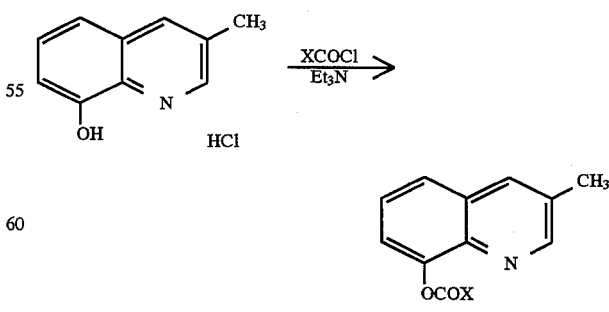

A mixture of the hydrochloride salt of 8-hydroxy-3-methylquinoline (10 g, 0.051 mol) and triethylamine (15.5 g, 0.15 mol) in 100 ml methylene chloride is treated with benzoyl chloride (10.8 g, 0.077 mol) at 0°–10° C. over 1 hour and is allowed to stir at room temperature for 3 hours. Water is added and the organic phase is washed with water 3 times and dried with magnesium sulfate. Evaporation and recrystalization from heptane/toluene gives the product as pale yellow crystals (8.8 g, 65% yield).

Other acylated 8-hydroxy-3-methylquinolines are prepared similarly.

EXAMPLE 2

Preparation of the Quaternary Salt

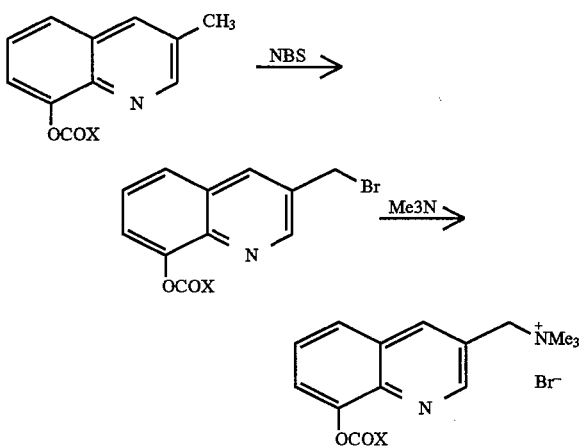

A solution of 8-acetoxy-3-methylquinoline (168.5 g, 0.84 mol), N-bromosuccinimide (NBS) (177.9 g, 1.00 mol), and 2,2'-azobisisobutyronitrile (AIBN) (6.7 g, 0.04 mol) in 1675 ml chlorobenzene is purged with nitrogen, heated at 80°–90° C. under nitrogen for 2 hours, cooled to room temperature and filtered. The filtrate is mixed with acetone (700 ml) and treated with trimethylamine (75.4 g, 1.28 mol) at 0°–5° C., allowed to stir at 5°–10° C. for 30 minutes and then at room temperature for 1 hour and filtered. The filter cake is washed with acetone and dried at 60° C. under vacuum to give a white solid (180 g, 63% overall yield). Highest yield achieved: 77%.

Other acylated 8-acetoxy-3-methylquinolines give the corresponding quaternary salts in similar yields.

Variation in Conditions and Critical Factors for Preparation of the Quaternary Salt (1) Chlorobenzene is the recommended solvent.
(2) Concentration can be as low as 0.2 g acetate per 10 ml solvent or as high as 1 g acetate per 10 ml solvent. It can presumably be more concentrated as long as all reactants are soluble at reaction temperature.
(3) Temperature is generally restricted to 80°–95° C. Reaction is sluggish when temperature is below this range, and side reaction occurs when above this range.
(4) The amount of AIBN can be from 2%–10%.
(5) Reaction with trimethylamine is usually carried out −10°–10° C.
(6) The parent compound, 8-hydroxy-3-methylquinoline, inhibits the bromination. Thus its content should be limited below 5%.
(7) The bromination is carried out under nitrogen atmosphere. Oxygen can retard the reaction.

EXAMPLE 3

Preparation of 8-Hydroxy-3-Methoxymethylquinoline

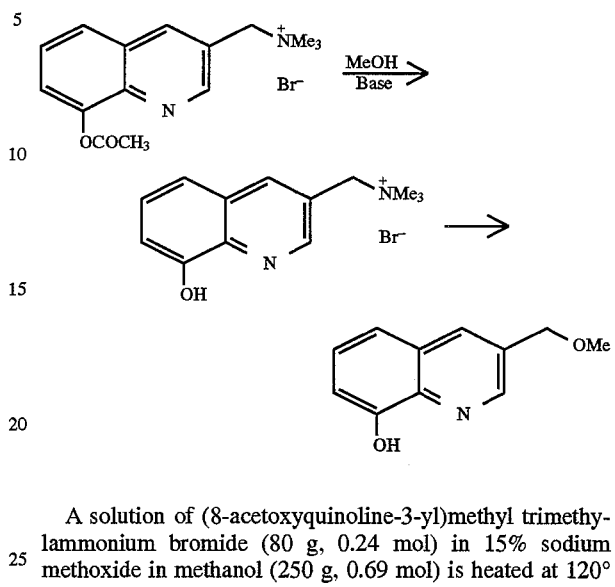

A solution of (8-acetoxyquinoline-3-yl)methyl trimethylammonium bromide (80 g, 0.24 mol) in 15% sodium methoxide in methanol (250 g, 0.69 mol) is heated at 120° C. in a pressure reactor for 18 hours and concentrated under reduced pressure. The residue is diluted with water and the pH is adjusted to 7–8 and filtered. The filter cake is washed with water and dried at 60° C. under vacuum to give a tan solid (40.63 g, 91% yield).

Examples 4–17 illustrate the methoxylation reaction using varied conditions. A methanol solution of the quaternary ammonium bromide and 3 equivalents of base, optionally with a catalyst, is heated at 65°–180° C. in a closed reactor for 16–96 hours and concentrated under reduced pressure. The residue is diluted with water and the pH is adjusted to 7–8 and filtered. The filter cake is washed with water and dried at 60° C. under vacuum to give a tan solid product.

| Examples | Conditions | Time (Hrs.) | Yields |
|---|---|---|---|
| 4 | no catalyst, NaOMe, 65° C. | 31 | 4% |
| 5 | no catalyst, LiOMe, 65° C. | 31 | 50% |
| 6 | 5% $CuSO_4$,NaOMe, 65° C. | 31 | 65% |
| 7 | 10% $CuSO_4$,NaOMe, 65° C. | 22 | 94% |
| 8 | 10% $CuSO_4$,$K_2CO_3$,65° C. | 96 | 73% |
| 9 | 50% $CuSO_4$,$K_2CO_3$,65° C. | 47 | 98% |
| 10 | 5% $FeSO_4$,$K_2CO_3$,65° C. | 96 | 67% |
| 11 | 10% $ZnCl_2$,NaOMe, 65° C. | 20 | 38% |
| 12 | 1–2% $CuSO_4$,$K_2CO_3$,150° C. | 22 | 69–91% |
| 13 | 1–2% $CuSO_4$,NaOMe, 120° C. | 17–21 | ~80% |
| 14 | no catalyst, 13% NaOMe, 120° C. | 19 | 73% |
| 15 | no catalyst, 15% NaOMe, 120° C. | 18 | 74% |
| 16 | no catalyst, NaOMe, 150° C. | 17 | 73% |
| 17 | no catalyst, NaOMe, 180° C. | 16 | 69% |
| 18 | no catalyst, $K_2CO_3$, 150° C. | 16.5 | 65% |

When X of formula IV=Ph, a crude yield of 82% of the final product is obtained after heating the quaternary salt with potassium carbonate in methanol at 150° C. for 18 hours.

When X of formula IV=OMe, a crude yield of 90% of the final product is obtained after heating the quaternary salt with potassium carbonate in refluxing methanol in the presence of 10% $CuSO_4$ for 22 hours.

Variation in Conditions and Critical Factors for the Methoxylation (1) Transition metal salts such as but not limited to CuSO$_4$, FeSO$_4$, ZnSO$_4$, ZnCl$_2$ catalyze the reaction.

(2) Temperature of the process may vary from 65° C. to 180° C. Higher temperature may cause side-reaction. At lower temperature, the reaction may be very sluggish.

(3) Methanol is the preferred solvent. Diglyme or DMSO, along with NaOMe may also be used as a solvent.

(4) Sodium methoxide and potassium carbonate are preferred for the reaction although other bases, such as LiOMe, KOMe, Ca(OMe)$_2$, Mg(OMe)$_2$, NaHCO$_3$, Na$_2$CO$_3$, KHCO$_3$, CaCO$_3$, Me$_3$N, Et$_3$N, and pyridine can be used under appropriate conditions, such as higher temperature. In fact, the reaction may be carried out without added base since it produces base (Me$_3$N) during the reaction course.

(5) Concentration is not critical. The highest concentration used was 15% NaOMe, or 3 g quaternary salt per 10 ml methanol, and the lowest was 0.2 g quaternary salt per 10 ml methanol.

What is claimed is:

1. A compound of the formula

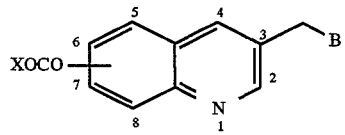

wherein X is straight or branched C$_1$–C$_6$ alkyl, phenyl, —O—C$_1$–C$_4$ straight or branched alkyl

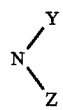

wherein Y and z are independently H, straight or branched C$_1$–C$_6$ alkyl or phenyl and B is halogen, or a quaternary ammonium halide.

2. A compound according to claim 1 wherein X is —CH$_3$ in the 8 position and B is bromine.

3. A compound according to claim 1 wherein X is —CH$_3$ in the 8 position and B is a quaternary ammonium bromide.

4. A compound according to claim 1 wherein X is phenyl and B is bromine.

5. A compound according to claim 1 wherein X is phenyl and B is quaternary ammonium bromide.

6. A compound according to claim 1 wherein X is t-butyl butyl and B is bromine.

7. A compound according to claim 1 wherein X is t-butyl butyl and B is quaternary ammonium bromide.

8. A compound according to claim 1 wherein X is —OCH$_3$ in the 8 position and B is bromine.

9. A compound according to claim 1 wherein X is —OCH$_3$ and B is quaternary ammonium bromide.

10. A compound of the formula

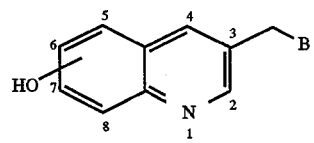

wherein B is a quaternary ammonium halide.

11. A compound according to claim 10 wherein the OH is in the 8 position and B is quaternary ammonium bromide.

12. A process for preparing a compound of the formula

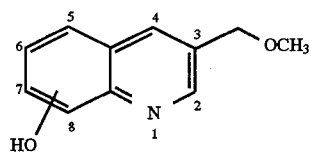

which comprises reacting a compound of the formula

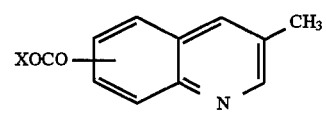

wherein X is straight or branched C$_1$–C$_6$ alkyl, phenyl, —O—C$_1$–C$_4$ straight or branched alkyl or

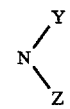

wherein Y and Z are independently H, straight or branched C$_1$–C$_6$ alkyl or phenyl with a radical halogenating reagent wherein the halogen is bromine or chlorine to form a compound of the formula

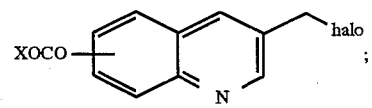

reacting compound III with a tertiary amine without a reactive beta-hydrogen to form a compound of the formula

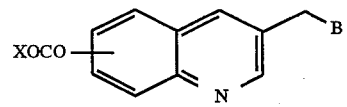

wherein B is a quaternary ammonium halide; and reacting compound IV with a base in methanol at a temperature within the range of about 120° to about 180° C. in a closed reactor to form a compound of formula I; or reacting compound IV with a base in methanol in the presence of a transition metal salt at a temperature within the range of about 65° C. to about 180° C. in a closed reactor to form a compound of formula I.

13. A process according to claim 12 wherein OH of compound I is in the 8 position, the radical halogenating agent to form compound III is N-bromosuccinimide, the tertiary amine to form compound IV is trimethyl amine and compound IV is reacted with sodium methoxide in methanol in the presence of $CuSO_4$ at a temperature within the range of about 65° C. to about 180° C.

14. A process according to claim 13 wherein the reaction temperature is about 65° C. in the presence of $CuSO_4$ to form compound I from compound IV.

15. A process according to claim 12 wherein the acylating agent to form compound II is acetic anhydride, the radical halogenating agent to form compound III is N-bromosuccinimide, the tertiary amine to form compound IV is trimethyl amine and compound IV is reacted with sodium methoxide in methanol at a temperature of about 120° C.

* * * * *